(12) United States Patent
Eckhardt et al.

(10) Patent No.: US 8,632,665 B2
(45) Date of Patent: Jan. 21, 2014

(54) ELECTROCHEMICAL SENSOR WITH DIFFUSION LABYRINTH

(75) Inventors: Rolf Eckhardt, Alzenau (DE); Martin Weber, Meckenheim (DE)

(73) Assignee: MSA Auer GmbH, Berlin (DE)

( * ) Notice: Subject to any disclaimer, the term of this patent is extended or adjusted under 35 U.S.C. 154(b) by 0 days.

(21) Appl. No.: 12/992,148

(22) PCT Filed: May 7, 2009

(86) PCT No.: PCT/EP2009/055535
§ 371 (c)(1),
(2), (4) Date: Jan. 10, 2011

(87) PCT Pub. No.: WO2009/138357
PCT Pub. Date: Nov. 19, 2009

(65) Prior Publication Data
US 2011/0100811 A1    May 5, 2011

(30) Foreign Application Priority Data
May 15, 2008  (DE) .................. 10 2008 024 392

(51) Int. Cl.
*G01N 27/413*      (2006.01)
(52) U.S. Cl.
USPC ........... 204/415; 204/409; 204/416; 204/431; 204/432
(58) Field of Classification Search
USPC ..................... 204/409, 412, 415, 431–432
See application file for complete search history.

(56) References Cited

U.S. PATENT DOCUMENTS

| 3,328,277 | A | 6/1967 | Solomons et al. |
| 3,613,981 | A | 10/1971 | Ramseier |
| 4,406,770 | A | 9/1983 | Chan et al. |
| 5,114,561 | A | 5/1992 | Bannister |
| 5,723,036 | A | 3/1998 | Chrzan et al. |
| 5,830,337 | A | 11/1998 | Xu |
| 5,932,079 | A | 8/1999 | Haupt et al. |
| 6,082,714 | A * | 7/2000 | Dornfest et al. ............ 261/142 |
| 6,358,384 | B1 | 3/2002 | Warburton |
| 6,666,963 | B1 | 12/2003 | Peng et al. |
| 7,258,773 | B2 | 8/2007 | Zhou et al. |
| 7,608,177 | B2 | 10/2009 | Nauber et al. |
| 2002/0070112 | A1 | 6/2002 | Lee et al. |
| 2006/0021873 | A1 | 2/2006 | Mett |

FOREIGN PATENT DOCUMENTS

| DE | 1962293 | | 12/1969 |
| DE | 2547613 | A1 | 10/1975 |
| DE | 2547613 | A1 | 4/1977 |
| DE | 4231256 | A1 | 3/1994 |

(Continued)

OTHER PUBLICATIONS

Vetter, "Electrochemical Kinetic", 1961, Springer Verlag.

(Continued)

*Primary Examiner* — Bach Dinh
(74) *Attorney, Agent, or Firm* — The Webb Law Firm

(57) ABSTRACT

The invention relates to an electrochemical sensor including a housing with a chamber containing an electrolyte, at least one measuring electrode for oxygen detection, at least one counter electrode and at least one reference electrode, wherein the sensor has a two-part diffusion barrier, wherein a first part of the barrier forms a labyrinth with a second part of the barrier disposed between the measuring and the counter electrode.

17 Claims, 3 Drawing Sheets

(56) References Cited

FOREIGN PATENT DOCUMENTS

| DE | 19726453 A1 | 1/1999 |
|---|---|---|
| DE | 19845318 A1 | 4/2000 |
| DE | 102004037312 A1 | 3/2006 |
| DE | 102004059280 A1 | 6/2006 |
| EP | 1600768 A1 | 11/2005 |
| EP | 2286210 | 8/2011 |
| GB | 2049952 A | 12/1980 |
| WO | 8909398 A1 | 10/1989 |
| WO | 2007115801 A1 | 10/2007 |
| WO | 2009-138357 | 11/2009 |

OTHER PUBLICATIONS

Yan et al., "Solid Polymer Electrolyte-Based Electrochemical Oxygen Sensor", Sensors and Actuators, 1989, pp. 33-40, vol. 19.

Osada et al., "Polymer Sensors and Actuators", Chap. 1 Ion Conducting Polymer Sensors, pp. 10-13.

Labyrinth—Wikipedia.

* cited by examiner

ELECTROCHEMICAL SENSOR WITH DIFFUSION LABYRINTH

BACKGROUND OF THE INVENTION

1. Field of the Invention

The present invention relates to an electrochemical sensor, which has a two-part diffusion barrier, wherein a first part of the barrier forms a labyrinth with a second part of the barrier said barrier located between the measuring and counter electrode. This diffusion barrier is particularly useful in a lead-free electrochemical oxygen sensor.

2. Description of the Related Art

The market standard for oxygen sensors is a simple two-electrode sensor, in which the cathode is an expendable block of lead. The service life of these sensors depends firstly on the quantity of lead they contain and secondly on the mass flow control of oxygen to the measuring electrode. The service life is typically between one and three years. Apart from the fixed service life, another disadvantage of this type of sensor is the use of lead because of its potentially hazardous nature. This has resulted in numerous attempts to develop lead-free oxygen sensors. Sensors that use metals other than lead in a consumptive reaction (e.g. modified zinc-air batteries) must be explicitly excluded at this point, as must those that work with metal oxide electrolytes at high temperatures (e.g. lambda sondes) because the invention does neither cover a consumptive sensor nor a sensor that needs high operation temperatures (high means above 120° C.). For some time now, the companies Dräger and RAE Systems have had oxygen sensors on the market that function at ambient temperatures (−40° C. to 60° C.) according to the oxygen pump principle. In these sensors, oxygen is reduced to $O^{2-}$ (which further reacts to form water) at the measuring electrode (ME) and at the counter electrode (CE) $O^{2-}$ (from water) is oxidised to form oxygen gas. As a result the mass balance is set. This kind of sensor, however, needs a third electrode, a reference electrode (RE), against which the measuring electrode potential is maintained within a range of −300 to −800 mV. This sensor working principle is documented in numerous patents and patent applications. One of the first patents is U.S. Pat. No. 3,328,277A from the company Honeywell in 1964, in which a lead-free oxygen sensor is operated with a scavenger electrode. Further descriptions of measuring cells, which can also be used to measure gaseous oxygen, come from Dräger in the 1990's (DE 4231256 C2 and DE 1962293 C1). These firstly describe the use of different metals in the measuring electrodes and secondly identify a platinum-oxygen electrode as the stable reference electrode. The range of metals used for oxygen reduction can be extended to include other platinum metals, such as iridium, for example. However, the use of a Pt air-oxygen electrode as a reference electrode was suggested in the textbook *Elektrochemische Kinetik* written by Prof. Dr. K. Vetter in the 1960's (K. Vetter, *Elektrochemische Kinetik*, Springer Verlag, 1961), in which the author described $O_2$ reduction on platinum surfaces. A Nernst correlation between the $O_2$ partial pressure and the reduction potential, which patent DE 4231256 C2 wants to avoid, can therefore be excluded as improbable for standard customary electrodes.

More recent patents and patent applications deal with finding a solution to the central problems involved in constructing a lead-free $O_2$ sensor, namely, maintaining an oxygen concentration gradient between the ME and the CE and also removing the $O_2$ gas produced at the CE (to prevent back diffusion of $O_2$ to the ME). The Dräger patent DE 19726453 C2 describes how the ME is protected by a fourth electrode from back diffusion of dissolved $O_2$ gas in the electrolyte. Patent DE 19845318 C2, which follows a similar line, aims to achieve this effect using sintered electrodes. U.S. Pat. No. 6,666,963 B1 from Industrial Scientific claims that gases occurring in the sensor are removed via a pressure-compensating system. In this case, the distance required between the ME and the CE is obtained by locating the electrodes at opposite ends of the sensor.

The latest direction taught in the patent literature involves increasing the robustness of the sensors. This firstly increases their service life and breadth of application and, secondly, opens up the possibility of miniaturizing gas sensors while maintaining or improving their performance. Published patent application DE 102004037312 A1 from Drager describes the construction of a very flat sensor using ionic liquids as the electrolyte. Drager's patent DE 102004059280 B4 specifically describes a flat $O_2$ gas sensor, in which the ME is protected from $O_2$ back diffusion with a Nafion membrane and is also provided with an integrated memory chip. U.S. Pat. No. 7,258,773 B2 from RAE Systems works with Nafion as the solid electrolyte, to ensure there are no leaks. Protection from back-diffusion of gas to the ME occurs here too. The construction of oxygen sensors with Nafion membranes is clearly taught in Y. Osada, D.E. DeRossi, *Polymer Sensors and Actuators*, Springer (2000); original source: H.Q. Yan, J.T Lu (1989) Sensors and Actuators 19:33.

A more recent sensor is presented in published patent application WO 2007/115801 A1 from MST-Technology. Here, the ME and CE are on one level in the sensor. The ME is in contact with the outside world through a gas diffusion barrier; the CE is characterised by a plurality of openings designed to remove the oxygen gas generated. The ME is surrounded by a barrier placed concentrically around it. This concentric barrier is used to increase the distance between the ME and CE, which is necessary in order to create an $O_2$ concentration gradient. The back-diffusion of $O_2$ into the solution is thereby prevented.

One disadvantage of this simple, concentric barrier, however, is that a large number of components is required, since the ME and CE cannot be combined in a single component. The need for several components increases the probability of manufacturing errors and complicates the structure. Furthermore, only a relatively small increase in distance is possible with this simple, concentric barrier. In order to guarantee a stable gradient, the diffusion distance between the ME and CE must be of a certain minimum length.

SUMMARY OF THE INVENTION

The present invention provides an electrochemical sensor requiring less components, whereby making the design simpler and the operation of the sensor more reliable and robust. It is also desirable to provide a greater distance between the CE and ME using a diffusion barrier while still maintaining a small, compact sensor.

These advantages are achieved by an electrochemical sensor in accordance with the present invention. While these advantages can be achieved in various electrochemical sensors, including $H_2S$, $H_2$ and CO as well as oxygen, the benefits will be described primarily in relation to an oxygen sensor. Generally the present invention comprises an electrochemical oxygen sensor (1), consisting of a housing (11) with a chamber containing an electrolyte (9), at least one measuring electrode (2a) for analyte detection, at least one counter electrode (2b) and at least one reference electrode (7), as well as an opening (4) which controls the mass flow (flux) of oxygen to the measuring electrode (2a) and at least one ventilation opening (5) at the counter electrode (2b) (and additional ventilation openings (10), if necessary), characterized in that the sensor (1) has a two-part diffusion barrier, wherein a first part (12) of the barrier forms a labyrinth shape with a second part (6) of the barrier, disposed between the measuring and the counter electrode (2a, 2b).

For functional reasons, there must be a diffusion gap between the ME and CE, across which an analyte gradient can be formed. In the case of an oxygen sensor, the gradient has a value of zero for the oxygen concentration at the ME and, typically, >20.9% at the CE. Gaseous oxygen is thereby reduced to water at the ME; the oxygen anion in the water is oxidised to oxygen gas at the CE. The reaction is maintained by a bias voltage of between −300 and −800 mV, which is applied between the reference electrode (RE) and ME. In order to prevent a potential shift at the RE, the RE should be located outside the gradient between the ME and CE.

DETAILED DESCRIPTION OF THE PREFERRED EMBODIMENT(S)

Figure 1:
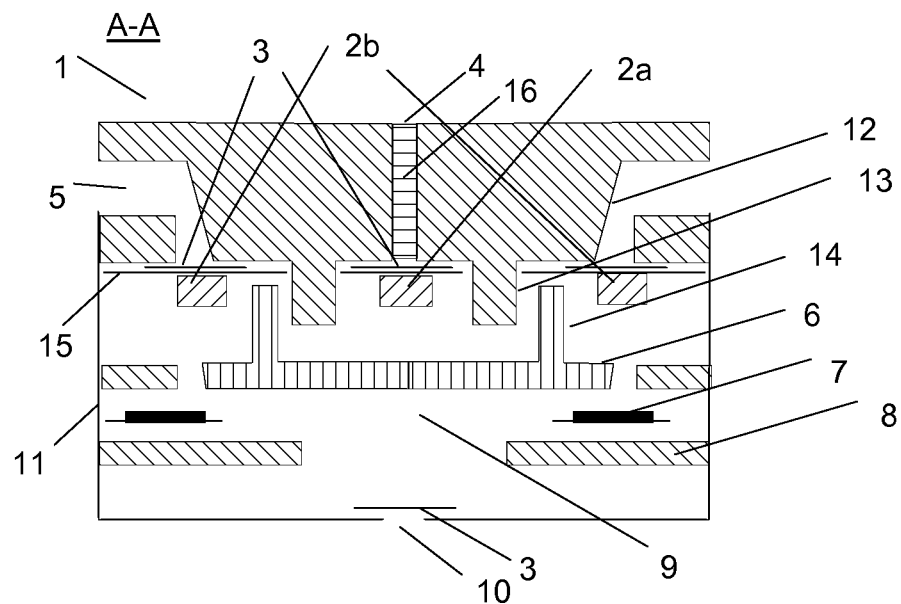
FIG. 1 is a schematic cross-sectional view of an electrochemical sensor wherein the walls of the first part and of the second part together form a wavelike channel in cross-section.

In one embodiment, the first part of the diffusion barrier (12) carries a membrane (15) with the measuring electrode (2a) and counter electrode (2b) on one level. Compared with most of the sensors described above, this sensor has the benefit that if the ME and CE are on one level in the sensor, the sensor can miniaturized more easily and the ohmic resistance (which is related to the sensor response time) can be minimized. The effective distance between the ME and CE, which is needed in order to create a sufficient $O_2$ concentration gradient, is produced by a labyrinth of semicircular, interlacing barriers.

The measuring electrode (2a) is preferably circular in design and the counter electrode (2b) is preferably an open or closed ring and these are disposed concentrically to one another. In case of the open ring for the CE an additional advantage is that the ME contact lead need not cross the CE, which in turn minimises the risk of an electrical short-circuit between the ME and CE.

The first part (12) and a second part (6) of the barrier preferably each have at least one essentially annular wall (13, 14) with a break in at least one section, which together form the diffusion labyrinth. In this case, it is preferable for the second part (6) of the barrier to have at least one annular wall (14) with a break in at least one section, wherein the walls of the first part (12) and those of the second part (6) are disposed in one another, such that the open section of an inner wall in each case faces an adjacent wall of the other part lying further outside.

In one embodiment of the electrochemical oxygen sensor (1), the walls (13, 14) of the first part (12) and those of the second part (6) together form a wavelike channel in cross-section (see FIG. 1). This facilitates the ME and CE being formed on one membrane, making it possible for both to be located on one part. Consequently, the sensor construction is simplified (having less parts) and can be manufactured less expensively. The same applies to an embodiment of the sensor using glass fibre separators or discs of solid electrolyte.

Figure 2:
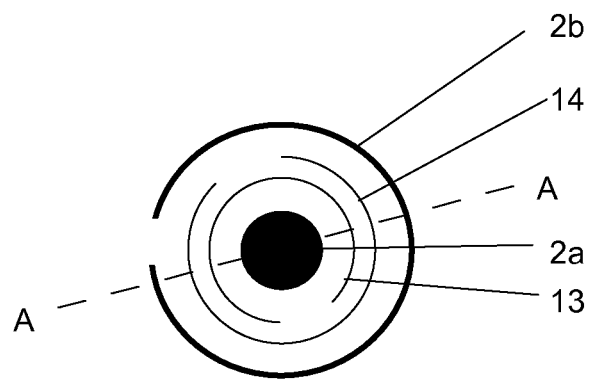
FIG. 2 is a schematic top view of the electrochemical sensor from FIG. 1.
Figure 3:
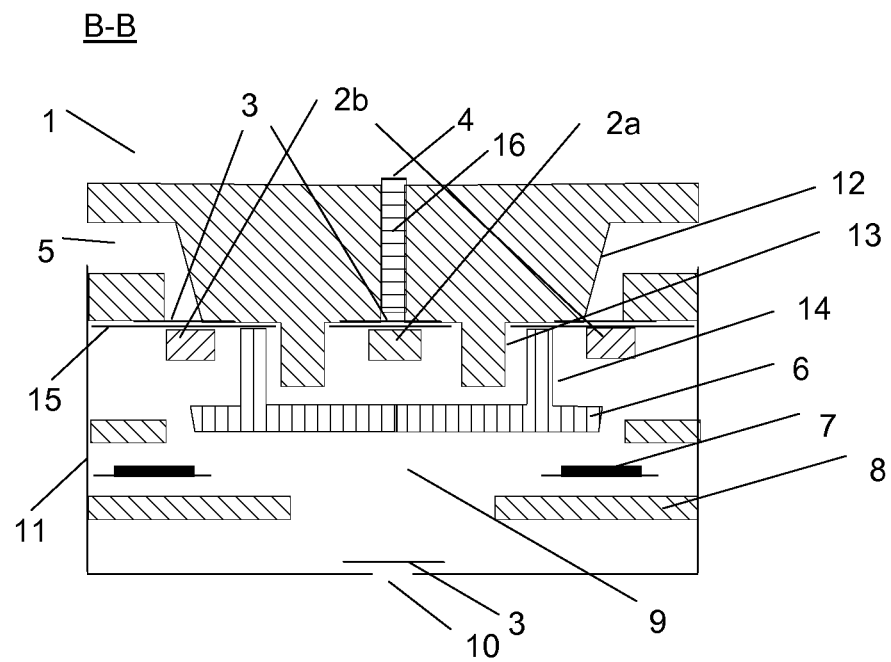
FIG. 3 is a schematic cross-sectional view of an electrochemical sensor, in which the walls of the first part are adjacent to the second part and the walls of the second part are adjacent to the first part of the diffusion barrier.
Figure 4:
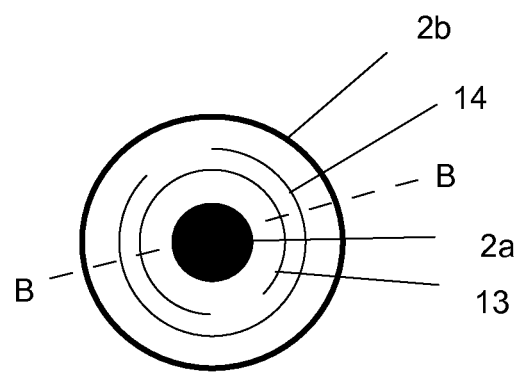
FIG. 4 is a schematic top view of the electrochemical sensor from FIG. 3.

Another embodiment is an electrochemical oxygen sensor (1), in which the walls (13) of the first part (12) are adjacent to the second part and the walls (14) of the second part (6) are adjacent to the first part of the barrier (see FIG. 2).

Figure 5:
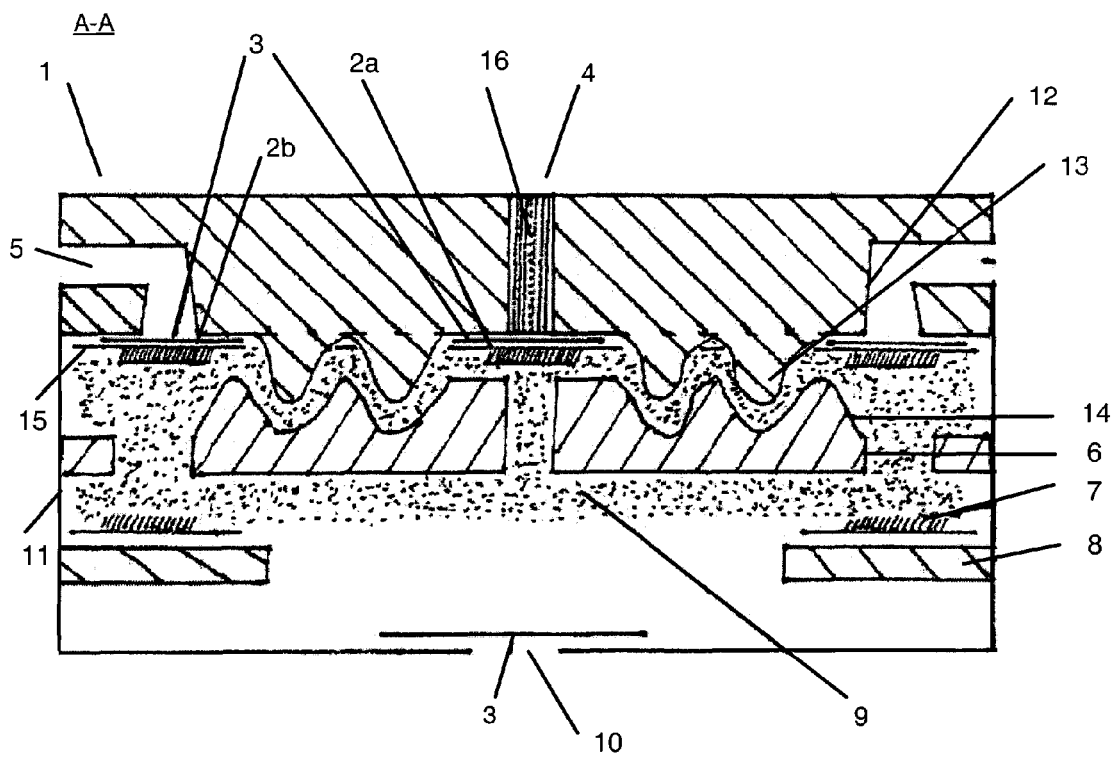
FIG. 5 is a schematic cross-sectional view of an electrochemical sensor, wherein the first part of the electrochemical sensor has two walls and the second part of the electrochemical sensor has three walls.
Figure 6:
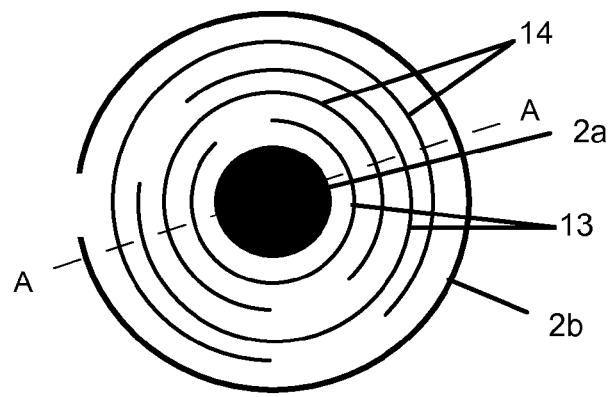
FIG. 6 is a schematic top view of the electrochemical sensor from FIG. 5.

To achieve a greater effective distance between the ME and the CE, it is preferable for the first part (12) and the second part (6) of the electrochemical oxygen sensor (1) to have at least two walls (13, 14) each (see FIGS. 5 and 6). Of course, more walls can be used to achieve an even greater effective distance.

In one embodiment of the electrochemical oxygen sensor (1), the at least one ventilation opening (5) at the counter electrode (2b) passes out of the oxygen sensor at the side. This protects it from becoming blocked by dirt and other material during field use. In a preferred embodiment, the ventilation openings (5) at the counter electrode (2b) are interconnected.

Preferably, the RE lies outside the $O_2$-concentration—gradient between the ME and CE and is unaffected by the gradient, which provide for a stable RE, even after years of use.

The materials used for the electrodes (2a, 2b, 7) are known to those skilled in the art and are preferably chosen from the group made up of copper, silver, gold, nickel, palladium and platinum or oxides of these metals. The materials used for the individual electrodes can be the same or different. In one embodiment, the electrodes (2a, 2b, 7) are graphite electrodes, which are coated with materials from the group made up of copper, silver, gold, nickel, palladium and platinum or oxides of these metals. Again the materials used for each individual electrode can be the same or different. Particularly preferable is the use of materials from the group made up of gold, platinum, platinum oxide and mixtures of platinum and platinum oxide.

In a preferred embodiment of the electrochemical oxygen sensor (1), the membrane (15) on which the measuring and counter electrode (2a, 2b) are located is gas-permeable.

It is further preferable for at least one of the openings (4), (5) and (10) to be closed off by a gas-permeable seal (3). At least one of the openings (4), (5) and (10) is preferably sealed off by a polytetrafluoroethylene (PTFE) film.

It is likewise preferable for the opening which controls mass flow (4) to be a diffusion barrier. This diffusion barrier (16) is preferably selected from the group of capillaries, membranes or films. It is particularly preferable for this opening use a capillary as the diffusion barrier (16).

To create a capillary, it is possible to simply drill a hole in the first part (12) of the diffusion barrier. A minimum hole cross-section of roughly 100 μm can be achieved with a length of 2 mm using a conventional drill. However, the risk of the bit breaking off is very high and bits are comparatively expensive. Smaller holes can be made using laser drills.

Certain applications make it necessary to dispense with capillary mass flow control and instead use a leak-proof film in conjunction with a prepared opening, in order to obtain a partial-pressure-dependent oxygen sensor. This is used primarily in medical technology (the functioning of the human lung is also $O_2$ partial pressure dependent). In relation to the films, which may be used as a diffusion barrier (16) at the opening which controls the mass flow (4), films from the group made up of fluorinated ethylene propylene (FEP), polyethylene (PE), polypropylene (PP), polymethyl methacrylate (PMMA), polyethylene terephthalate (PET) polyaryletheretherketone (PEEK) and polytetrafluorinated ethylene (PTFE).

In another preferred embodiment, the mass flow control opening (4) is a Knudsen membrane.

In one embodiment of the electrochemical sensor (1) the electrolyte is an aqueous solution with an acidic or basic pH-value.

The electrolyte should preferably be securely contained within the sensor to guarantee the sensor's functionality. Several embodiments are possible for this. In one embodiment of the present invention, the electrolyte is maintained in an absorbent medium, chosen from the group made up of glass fibre mats, plastic discs or silica gel. Alternatively the electrolyte can be present as an acid-soaked silica gel. In another embodiment, the electrolyte is present in the form of an acidic, electroconductive gel. Still another alternative is the use of glass fibre fleeces soaked with sulphuric acid or other acids.

Another advantage of the sensor according to the present invention is its very open design. For example, the use of a plurality of ventilation openings means that pressure can easily escape from the sensor. This is particularly important in an oxygensensor given the fact that oxygen is continuously being produced at the CE and must be immediately removed, in order to preclude the adverse consequences of high internal pressures (such as signal fluctuations and leaks) from the very outset. The effect of pressure waves and rapid pressure fluctuations should also be minimized with this design. These advantages can also be achieved by using vents in various other electrochemical sensors, including $H_2S$, $H_2$ and CO as well as oxygen.

The invention claimed is:

1. An electrochemical sensor, comprising
a housing with a chamber containing an electrolyte,
at least one measuring electrode for analyte detection,
at least one counter electrode and at least one reference electrode, as well as
an opening which controls mass flow to the measuring electrode,
wherein the sensor has a two-part diffusion barrier, wherein a first part of the barrier forms a labyrinth with a second part of the barrier disposed between the measuring and the counter electrode, and
wherein the first part of the diffusion barrier carries a membrane, the measuring electrode and the counter electrode are formed on the membrane, and the measuring electrode and the counter electrode are on one horizontal level.

2. The electrochemical sensor according to claim 1, wherein the sensor is an oxygen sensor.

3. The electrochemical sensor according to claim 2, further comprising at least one ventilation opening at the counter electrode.

4. The electrochemical sensor according to claim 2, wherein the measuring electrode is circular in design, the counter electrode is an open or closed ring, and the measuring electrode and the counter electrode are disposed concentrically to one another.

5. The electrochemical sensor according to claim 2, wherein the first part and the second part of the two-part diffusion barrier each have at least one essentially annular wall with a break in at least one section, which together form the diffusion labyrinth.

6. The electrochemical sensor according to claim 1, further comprising at least one ventilation opening at the counter electrode.

7. The electrochemical sensor according to claim 6, wherein the measuring electrode is circular in design, the counter electrode is an open or closed ring, and the measuring electrode and the counter electrode are disposed concentrically to one another.

8. The electrochemical sensor according to claim 6, wherein the first part and the second part of the two-part diffusion barrier each have at least one essentially annular wall with a break in at least one section, which together form the diffusion labyrinth.

9. The electrochemical sensor according to claim 1, wherein the measuring electrode is circular in design, the counter electrode is an open or closed ring, and the measured electrode and the counter electrode are disposed concentrically to one another.

10. The electrochemical sensor according to claim 1, wherein the measuring electrode is circular in design, the counter electrode is an open or closed ring, and the measuring electrode and the counter electrode are disposed concentrically to one another.

11. The electrochemical sensor according to claim 1, wherein the first part and the second part of the two-part diffusion barrier each have at least one essentially annular wall with a break in at least one section, which together form the diffusion labyrinth.

12. The electrochemical sensor according to claim 1, wherein the second part of the two-part diffusion barrier has at least one annular wall with a break in at least one section, and wherein walls of the first part and walls of the second part are disposed in one another, such that an open section of an inner wall in each case points to an adjacent wall of another part lying further outside.

13. The electrochemical sensor according to claim 1, wherein walls of the first part and walls of the second part together form a wavelike channel in cross-section.

14. The electrochemical sensor according to claim 1, wherein walls of the first part are adjacent to the second part and walls of the second part are adjacent to the first part of the barrier.

15. The electrochemical sensor according to claim 1, wherein the first part and the second part have at least two walls each.

16. The electrochemical sensor according to claim 1, wherein at least one ventilation opening at the counter electrode passes out of the sensor at the side.

17. The electrochemical sensor according to claim 1, wherein ventilation openings at the counter electrode are interconnected.

* * * * *

UNITED STATES PATENT AND TRADEMARK OFFICE
CERTIFICATE OF CORRECTION

| | | |
|---|---|---|
| PATENT NO. | : 8,632,665 B2 | Page 1 of 1 |
| APPLICATION NO. | : 12/992148 | |
| DATED | : January 21, 2014 | |
| INVENTOR(S) | : Rolf Eckhardt et al. | |

It is certified that error appears in the above-identified patent and that said Letters Patent is hereby corrected as shown below:

In the Claims

Column 6, Line 27, Claim 10, "claim 1" should read -- claim 3 --

Column 6, Line 24, Claim 9, delete "measured" and insert -- measuring --

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,632,665 B2
APPLICATION NO.  : 12/992148
DATED            : January 21, 2014
INVENTOR(S)      : Eckhardt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 4 days.

Signed and Sealed this
Twenty-second Day of September, 2015

Michelle K. Lee
*Director of the United States Patent and Trademark Office*